US00PP11444P

United States Patent [19]

Kientzler

[11] Patent Number: Plant 11,444

[45] Date of Patent: Jul. 11, 2000

[54] NEW GUINEA IMPATIENS PLANT NAMED 'KISAUL'

[75] Inventor: Ludwig Kientzler, Gensingen, Germany

[73] Assignee: Paul Ecke Ranch, Inc., Encinitas, Calif.

[21] Appl. No.: 09/127,637

[22] Filed: Jul. 31, 1998

[51] Int. Cl.[7] ..... A01H 5/00

[52] U.S. Cl. ..... Plt./318

[58] Field of Search ..... Plt./318

[56] References Cited

U.S. PATENT DOCUMENTS

P.P. 10,303 3/1998 Keintzler ..... Plt./318

*Primary Examiner*—Howard J. Locker
*Assistant Examiner*—Wendy A Baker
*Attorney, Agent, or Firm*—C. A. Whealy

[57] ABSTRACT

A new and distinct cultivar of New Guinea Impatiens plant named 'Kisaul', characterized by its bright red-colored flowers; uniformly upright and somewhat spreading growth habit; very freely branching, dense and bushy plant habit; and very dark green leaves.

1 Drawing Sheet

BACKGROUND OF THE INVENTION

The present invention relates to a new and distinct cultivar of New Guinea Impatiens plant, botanically known as *Impatiens hawkeri*, and hereinafter referred to by the cultivar name Kisaul.

The new cultivar is a product of a planned breeding program conducted by the Inventor in Gensingen, Germany. The objective of the breeding program was to develop early-flowering varieties with numerous flowers, uniform plant habit, attractive flower and foliage colors, and good flower form.

The new cultivar originated from a cross made by the Inventor of the proprietary selection identified as MF 117 as the male, or pollen parent, with the proprietary selection identified as MF 528 as the female, or seed parent.

The cultivar Kisaul was discovered and selected by the Inventor as a flowering plant within the progeny of the stated cross in a controlled environment in Gensingen, Germany, in April, 1996.

Asexual reproduction of the new cultivar by terminal cuttings taken at Gensingen, Germany, has shown that the unique features of this new Impatiens are stable and reproduced true to type in successive generations of asexual reproduction.

SUMMARY OF THE INVENTION

The following traits have been repeatedly observed and are determined to be the unique characteristics of 'Kisaul'. These characteristics in combination distinguish 'Kisaul' as a new and distinct cultivar:

1. Bright red-colored flowers.

2. Uniformly upright and somewhat spreading growth habit.

3. Very freely branching, dense and bushy plant habit.

4. Very dark green leaves.

Plants of the new New Guinea Impatiens are smaller, but have larger flowers than plants of the male parent, the proprietary selection identified as MF 117.

Plants of the new New Guinea Impatiens have bright red-colored flower and upper surfaces of leaves are very dark green whereas plants of the female parent, the proprietary selection identified as MF 528, have more orange-colored flowers and upper surfaces of leaves are reddish bronze.

Plants of the new New Guinea Impatiens are similar in flower color to plants of the cultivar Timor, disclosed in U.S. Plant Pat. No. 9,144. However, in side-by-side comparisons conducted in Encinitas, Calif., plants of the new New Guinea Impatiens differed from plants of the cultivar Timor in the following characteristics:

1. Plants of the new New Guinea Impatiens are less vigorous and spreading than plants of the cultivar Timor.

2. Plants of the new New Guinea Impatiens have smaller leaves than plants of the cultivar Timor.

3. Upper leaf surfaces of plants of the new New Guinea Impatiens are darker green than upper leaf surfaces of plants of the cultivar Timor. In addition, lower leaf surfaces of plants of the new New Guinea Impatiens are dark purple whereas lower leaf surfaces of plants of the cultivar Timor are green.

4. Flowers of plants of the new New Guinea Impatiens are smaller and less rounded than flowers of plants of the cultivar Timor.

5. Plants of the new New Guinea Impatiens have a more uniform flower display than plants of the cultivar Timor.

A detailed comparison of plants of 'Kisaul' and 'Timor' appears in Chart A at the end of the specification.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new New Guinea Impatiens.

The photograph at the top of the sheet comprises a top perspective view of a typical plant of 'Kisaul'.

The photograph at the bottom of the sheet comprises a comparison close-up view of typical flowers and leaves of the cultivars Kisaul (left) and Timor (right). Flower and foliage colors in the photographs may differ from the actual colors due to light reflectance.

DETAILED BOTANICAL DESCRIPTION

Plants of the cultivar Kisaul have not been observed under all possible environmental conditions. The phenotype may vary somewhat with variations in environment such as temperature and light intensity, without, however, any variance in genotype. The following observations, measurements and comparisons describe three plants measured separately in 25-cm hanging baskets in Encinitas, Calif., under commercial practice in a polyethylene-covered greenhouse with day temperatures ranging from 21 to 32° C. and night temperatures ranging from 16 to 18° C. and light levels of about 3,500 footcandles.

In the following description, color references are made to The Royal Horticultural Society Colour Chart except where general terms of ordinary dictionary significance are used.

Classification:

*Botanical.*—*Impatiens hawkeri* cultivar Kisaul.

*Commercial.*—New Guinea Impatiens cultivar Kisaul.

Parentage:

*Male parent.*—Proprietary selection of *Impatiens hawkeri identified as MF* 117.

*Female parent.*—Proprietary selection of *Impatiens hawkeri* identified as MF 528.

Propagation:

*Type cutting.*—Terminal cuttings.

*Time to initiate roots.*—Summer: About 14 days with 21° C. soil temperature. Winter: About 18 days with 21° C. soil temperature.

*Time to develop roots.*—Summer: About 21 days with 21° C. soil temperature. Winter: About 24 days with 21° C. soil temperature.

Plant description:

*Plant form.*—Uniformly upright and and somewhat spreading; "V"-shaped.

*Growth habit.*—Moderately vigorous. Very freely branching, dense and bushy growth. Appropriate for 10 to 25-cm containers.

*Crop time.*—From planting of a rooted cutting, about eight weeks are required to produce a finished flowering plant in a 12.5-cm container.

*Plant size.*—Height: About 24 cm. Width or spread: About 28 cm.

*Lateral branches.*—Quantity: About 9. Length: About 15 cm. Diameter: About 9 mm. Internode length: About 2.75 cm. Color: 59A.

*Foliage description.*—Leaves simple, generally symmetrical, abundant, opposite or in whorls, horizontal to plant. Mostly flat. Length: About 8.5 cm. Width: About 3.1 cm. Shape: Elliptic with acuminate apex, attenuate base and serrulate margin with ciliation. Texture: Smooth, matte. Color: Young foliage, upper surface: 137A. Young foliage, lower surface: 184B. Fully expanded foliage, upper surface: Darker than 139A. Fully expanded foliage, lower surface: 184A/184B. Venation, upper surface: 59A. Venation, lower surface: 59A. Petiole: Length: About 3.5 cm. Diameter: About 3 mm. Color: 59A.

Flower description:

*Flower type and habit.*—Bright red-colored flowers. Freely and continuously flowering. Flowers arise from leaf axils. Usually about 8 flowers and flower buds per lateral branch. Flowers positioned at the foliage and face upward and outward. Uppermost petal slightly cupped and flower shape is rounded rectangular. Flowers persistent.

*Flowering season.*—Year-round under greenhouse conditions. In the garden, flowering is continuous from spring until fall. Flowers typically last less than one week depending on environmental and cultural conditions.

*Flower size.*—Length, vertical axis: About 4 cm. Width, horizontal axis: About 4.5 cm. Depth: About 1.5 cm.

*Flower buds.*—Length: About 1.5 cm. Diameter: About 9 mm. Shape: Ovoid. Color: 40B.

*Petals.*—Quantity: Five. Length: Upper petal: About 2.5 cm. Middle petals: About 2 cm. Lower petals: About 2.5 cm. Width: Upper petal: About 4 cm. Middle petals: About 2.2 cm. Lower petals: About 2.5 cm. Shape: Cordate with acute base and entire margin. Texture: Velvety, slightly iridescent, smooth. Color: When opening, upper surface: More orange than 43A. When opening, lower surface: 40A. Fully opened, upper surface: 43A; color does not fade. Fully opened, lower surface: 41A.

*Spur.*—Length: About 4.4 cm. Shape: Narrow and curved. Color: 50A/50B.

*Peduncles.*—Length: About 5.25 cm. Angle: Upright. Strength: Strong. Color: 146B.

*Reproductive organs.*—Androecium: Stamen number: Five, anthers fused, filaments free. Anther shape: Obovate. Anther size: 3 mm by 5 mm. Anther color: 18B. Amount of pollen: Moderate. Pollen color: 8C. Gynoecium: Five-loculate fused. Pistil length: About 5 mm. Stigma color: 185D. Ovary color: 187A.

Disease resistance: Under commercial conditions, resistance to pathogens has not been observed.

Seed development: Seed production has not been observed.

CHART A

| CHARACTERISTIC | 'KISAUL' | 'TIMOR' |
|---|---|---|
| GROWTH HABIT, PLANT SHAPE | Upright and somewhat spreading | Upright and spreading |
| PLANT HEIGHT | About 24 cm | About 25 cm |
| PLANT WIDTH | About 28 cm | About 32 cm |
| VIGOR | Moderately vigorous | Vigorous |
| STEM COLOR | 59A | 146A with 60C blush |
| LEAF LENGTH | About 8.5 cm | About 9.5 cm |
| LEAF WIDTH | About 3.1 cm | About 4 |
| LEAF COLOR, MATURE, UPPER SURFACE | Darker than 139A | 147A |
| LEAF COLOR, MATURE, LOWER SURFACE | 184A/184B | 147C |
| PETIOLE LENGTH | About 3.5 cm | About 4.25 cm |
| PETIOLE COLOR | 59A | 63B/63C |
| FLOWER DIAMETER | About 4 by 5.5 cm | About 5.5 by 5.5 cm |
| PETAL COLOR, MATURE, UPPER SURFACE | 43A | Brighter than 40A; |
| PEDUNCLE LENGTH | About 5.25 cm | About 6 cm |
| PEDUNCLE COLOR | 146B | 144A |

It is claimed:

1. A new and distinct cultivar of New Guinea Impatiens plant named 'Kisaul', as illustrated and described.

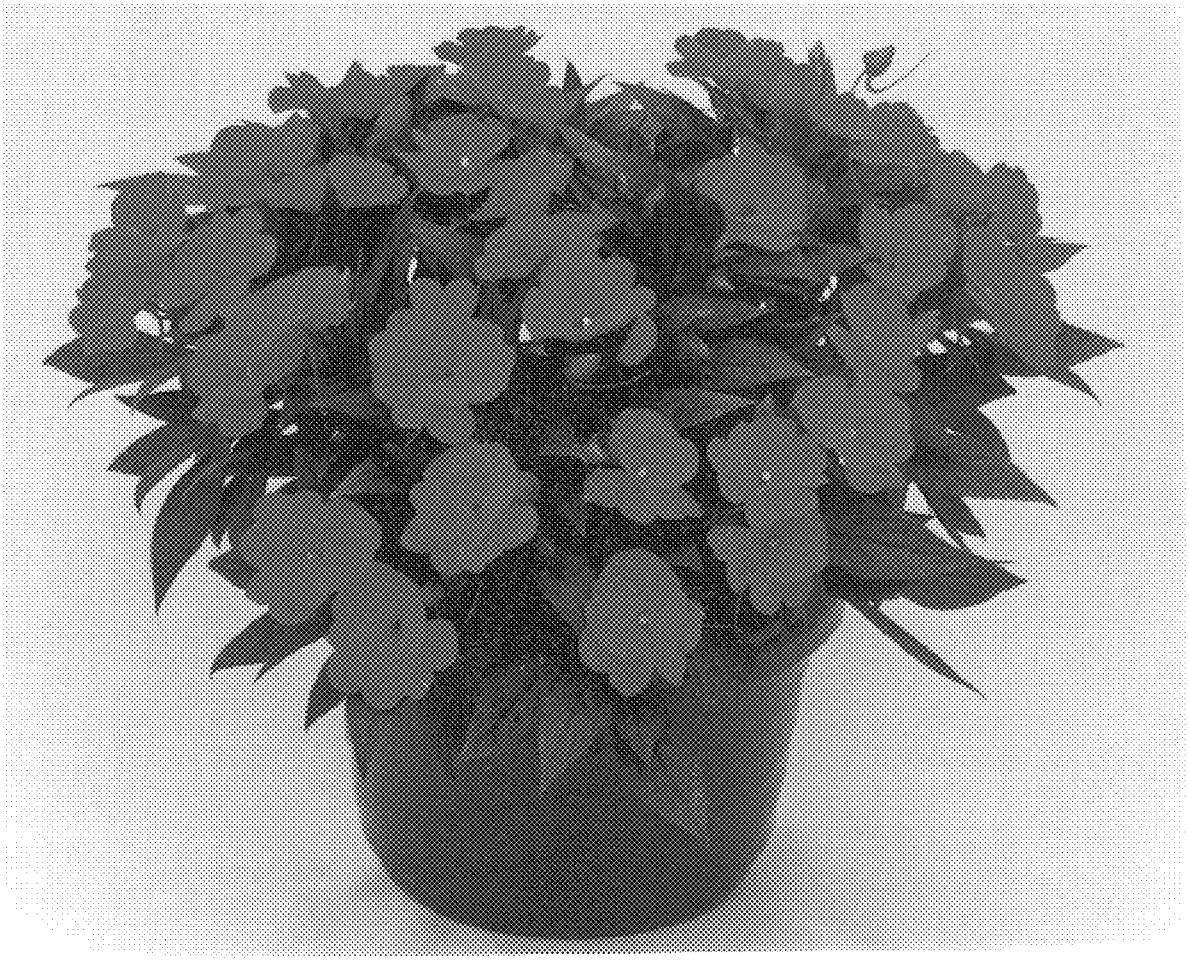
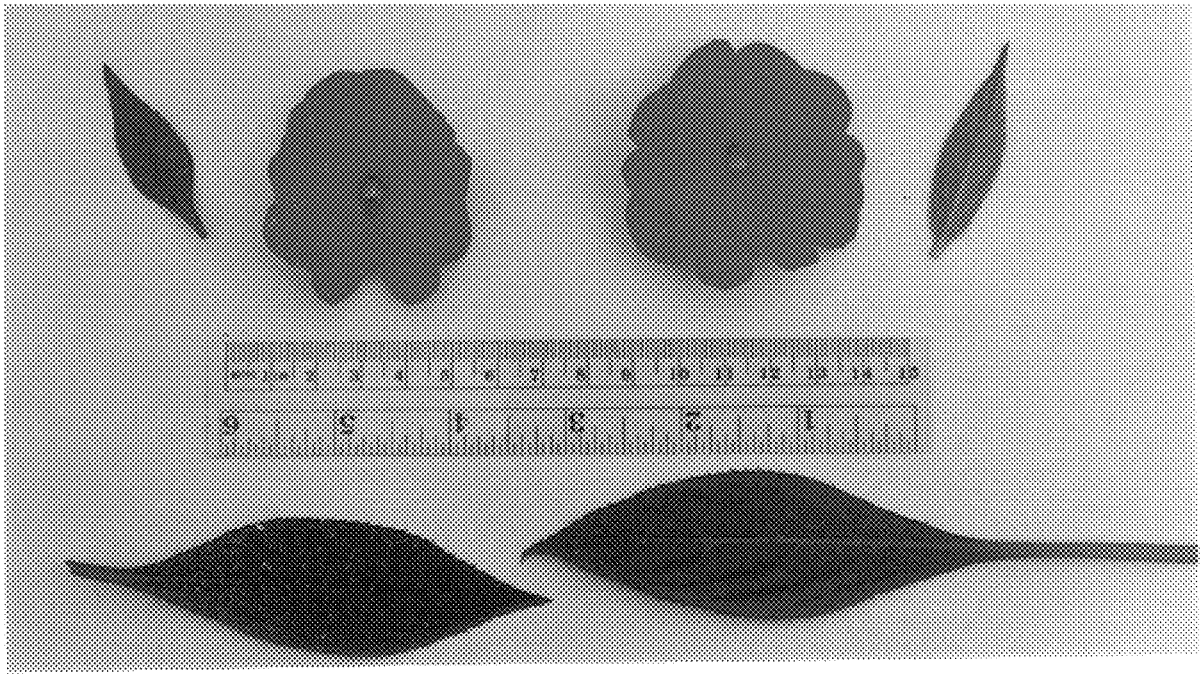

* * * * *